United States Patent
Brannan et al.

(10) Patent No.: US 10,716,619 B2
(45) Date of Patent: Jul. 21, 2020

(54) MICROWAVE AND RADIOFREQUENCY ENERGY-TRANSMITTING TISSUE ABLATION SYSTEMS

(71) Applicant: COVIDIEN LP, Mansfield, MA (US)

(72) Inventors: Joseph D. Brannan, Lyons, CO (US); Eric W. Larson, Littleton, CO (US)

(73) Assignee: COVIDIEN LP, Mansfield, MA (US)

( * ) Notice: Subject to any disclaimer, the term of this patent is extended or adjusted under 35 U.S.C. 154(b) by 198 days.

(21) Appl. No.: 15/626,867

(22) Filed: Jun. 19, 2017

(65) Prior Publication Data
US 2018/0360529 A1    Dec. 20, 2018

(51) Int. Cl.
*A61B 18/12* (2006.01)
*A61B 18/14* (2006.01)
(Continued)

(52) U.S. Cl.
CPC ...... *A61B 18/1482* (2013.01); *A61B 18/1206* (2013.01); *A61B 18/1815* (2013.01); *A61B 2017/00973* (2013.01); *A61B 2018/00011* (2013.01); *A61B 2018/00529* (2013.01); *A61B 2018/00577* (2013.01); *A61B 2018/00601* (2013.01); *A61B 2018/00607* (2013.01);
(Continued)

(58) Field of Classification Search
CPC ........... A61B 2018/00601; A61B 2018/00607; A61B 2018/00994; A61B 2018/1273; A61B 2018/1412; A61B 2018/1861; A61B 2018/1869; A61B 2018/1884; A61B 18/1482; A61B 18/1206; A61B 18/14; A61B 18/1815
See application file for complete search history.

(56) References Cited

U.S. PATENT DOCUMENTS

| D223,367 S | 4/1972 | Kountz |
| D263,020 S | 2/1982 | Rau, III |

(Continued)

FOREIGN PATENT DOCUMENTS

| DE | 390937 C | 3/1924 |
| DE | 1099658 B | 2/1961 |

(Continued)

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.

(Continued)

*Primary Examiner* — Daniel W Fowler (57) ABSTRACT

A surgical instrument for ablating tissue includes a handle portion and a shaft assembly extending distally from the handle portion. The shaft assembly includes an outer shaft, a coaxial cable extending through the outer shaft, and an electrode coupled to a distal portion of the outer shaft. The coaxial cable has a distal portion that forms a microwave antenna configured to transmit microwave energy radially outward and through the outer shaft. The electrode is configured to transmit radiofrequency energy. An actuation of the handle portion activates the transmission of the microwave energy from the microwave antenna and/or the transmission of the radiofrequency energy from the at least one electrode.

17 Claims, 9 Drawing Sheets

(51) Int. Cl.
*A61B 18/18* (2006.01)
*A61B 18/00* (2006.01)
*A61B 17/00* (2006.01)

(52) U.S. Cl.
CPC ............ *A61B 2018/00928* (2013.01); *A61B 2018/00946* (2013.01); *A61B 2018/00958* (2013.01); *A61B 2018/00982* (2013.01); *A61B 2018/00994* (2013.01); *A61B 2018/126* (2013.01); *A61B 2018/1253* (2013.01); *A61B 2018/1823* (2013.01); *A61B 2018/1838* (2013.01); *A61B 2018/1846* (2013.01); *A61B 2018/1853* (2013.01); *A61B 2218/002* (2013.01); *A61B 2218/007* (2013.01)

(56) References Cited

U.S. PATENT DOCUMENTS

| | | | |
|---|---|---|---|
| D266,842 S | 11/1982 | Villers et al. | |
| D278,306 S | 4/1985 | McIntosh | |
| 4,583,556 A | 4/1986 | Hines et al. | |
| 4,601,296 A * | 7/1986 | Yerushalmi | A61B 18/18 604/113 |
| D295,893 S | 5/1988 | Sharkany et al. | |
| D295,894 S | 5/1988 | Sharkany et al. | |
| D354,218 S | 1/1995 | Van de Peer | |
| 5,800,494 A | 9/1998 | Campbell et al. | |
| D424,693 S | 5/2000 | Pruter | |
| D424,694 S | 5/2000 | Tetzlaff et al. | |
| D425,201 S | 5/2000 | Tetzlaff et al. | |
| D449,886 S | 10/2001 | Tetzlaff et al. | |
| 6,355,034 B2 * | 3/2002 | Cosmescu | A61B 18/1402 606/41 |
| D457,958 S | 5/2002 | Dycus et al. | |
| D457,959 S | 5/2002 | Tetzlaff et al. | |
| 6,471,696 B1 * | 10/2002 | Berube | A61B 18/1492 606/33 |
| D487,039 S | 2/2004 | Webster et al. | |
| D496,997 S | 10/2004 | Dycus et al. | |
| D499,181 S | 11/2004 | Dycus et al. | |
| D525,361 S | 7/2006 | Hushka | |
| 7,101,369 B2 | 9/2006 | van der Welde | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al. | |
| D564,662 S | 3/2008 | Moses et al. | |
| D576,932 S | 9/2008 | Strehler | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| 7,797,056 B2 * | 9/2010 | Forde | A61B 18/1492 606/41 |
| 7,875,024 B2 | 1/2011 | Turovskiy et al. | |
| D634,010 S | 3/2011 | DeCarlo | |
| D681,810 S | 5/2013 | DeCarlo | |
| 9,379,444 B2 | 6/2016 | Bonn | |
| 9,439,730 B2 | 9/2016 | Rossetto | |
| 9,480,527 B2 | 11/2016 | Prakash et al. | |
| 9,498,285 B2 | 11/2016 | Behnke | |
| 9,526,557 B2 | 12/2016 | Brannan | |
| 9,526,568 B2 | 12/2016 | Ohri et al. | |
| 9,526,575 B2 | 12/2016 | Prakash et al. | |
| 9,549,778 B2 | 1/2017 | Shiu et al. | |
| 9,579,150 B2 * | 2/2017 | DeCarlo | A61B 18/1815 |
| 2004/0049254 A1 | 3/2004 | Longo | |
| 2005/0015081 A1 | 1/2005 | Turovskiy et al. | |
| 2008/0021486 A1 * | 1/2008 | Oyola | A61B 17/00491 606/169 |
| 2009/0163850 A1 * | 6/2009 | Betts | A61B 18/1492 604/21 |
| 2010/0106151 A1 * | 4/2010 | Longo | A61B 17/320016 606/33 |
| 2010/0125269 A1 * | 5/2010 | Emmons | A61B 18/1815 606/33 |
| 2010/0286687 A1 * | 11/2010 | Feldberg | A61B 18/18 606/33 |
| 2013/0067725 A1 * | 3/2013 | Behnke, II | A61B 18/1815 29/592.1 |
| 2013/0267943 A1 * | 10/2013 | Hancock | A61B 18/042 606/33 |
| 2014/0039491 A1 * | 2/2014 | Bakos | A61B 18/1492 606/41 |
| 2014/0296841 A1 | 10/2014 | Brannan | |
| 2014/0358140 A1 | 12/2014 | Emmons et al. | |
| 2015/0065964 A1 | 3/2015 | Ohri et al. | |
| 2015/0133910 A1 | 5/2015 | Brannan | |
| 2017/0100186 A1 | 4/2017 | Brannan et al. | |
| 2017/0207467 A1 * | 7/2017 | Shelton, IV | A61B 17/320092 |
| 2018/0261922 A1 * | 9/2018 | Behdad | A61B 18/1815 |
| 2018/0280084 A1 * | 10/2018 | Hancock | A61B 18/1445 |

FOREIGN PATENT DOCUMENTS

| | | |
|---|---|---|
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10217281 A1 | 10/2003 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 1159926 A3 | 3/2003 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |

(56) References Cited

FOREIGN PATENT DOCUMENTS

| | | |
|---|---|---|
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 56-161636 | 12/1981 |
| JP | 59-58933 | 4/1984 |
| JP | 5-5106 | 1/1993 |
| JP | 5-08933 | 2/1993 |
| JP | 05-40112 | 2/1993 |
| JP | 06343644 A | 12/1994 |
| JP | 07265328 A | 10/1995 |
| JP | H08-56955 | 5/1996 |
| JP | 08252263 A | 10/1996 |
| JP | 910223 | 1/1997 |
| JP | 09000492 A | 1/1997 |
| JP | 9117456 | 5/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2002253569 A | 9/2002 |
| JP | 2008142467 A | 6/2008 |
| KR | 20070093068 A | 9/2007 |
| KR | 20100014406 A | 2/2010 |
| KR | 20120055063 A | 5/2012 |
| SU | 166452 | 1/1965 |
| SU | 401367 A1 | 10/1973 |
| SU | 727201 A2 | 4/1980 |
| WO | 00/36985 A2 | 6/2000 |
| WO | 2010/035831 A1 | 4/2010 |

OTHER PUBLICATIONS

Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.

Bulletin of the American Physical Society, vol. 47, No. 5, Aug. 2002, p. 41.
C. F. Gottlieb et al., "Interstitial Microwave Hyperthermia Applicators having Submillimetre Diameters", Int J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas MedicalCenter,Chartotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSureTM" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite-Element Codes to Model Electrical Heating and Non-Linear Thermal Transport in Biological Media", Proc. ASME HTD-355, 131 (1997).

(56) References Cited

OTHER PUBLICATIONS

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSureTM Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSureTM Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSureTM System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
European Search Report dated Oct. 24, 2018, corresponding to European Application No. 18178349.9; 7 pages.
LigaSureTM Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences—Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Stagegaard, N., Petersen H.H., Chen X., Svendsen J.H., "Indication of the Radiofrequency Induced Lesion Size by Pre-ablation Measurements" Europace (2005) 7, 525-534.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: TargisTM Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.

(56) References Cited

OTHER PUBLICATIONS

Vallfors et al., "Automatically Controlled Bipolar Electrocoagulation—'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/136,098, filed Oct. 14, 1993; Roger A. Stern.
U.S. Appl. No. 08/483,742, filed Jun. 7, 1995; Roger A. Stern.
Australian Examination Report for application 2016200854 dated Sep. 9, 2016.
Japanese Office Action for application No. 2015-204490 dated Sep. 14, 2016.
Australian Examination Report for applicatoin No. 2015204318 dated Sep. 18, 2016.
Canadian Office Action dated Apr. 5, 2019, corresponding to counterpart Canadian Application No. 3,008,243; 4 total pages.

\* cited by examiner

MICROWAVE AND RADIOFREQUENCY ENERGY-TRANSMITTING TISSUE ABLATION SYSTEMS

BACKGROUND

1. Technical Field

The present disclosure relates to a tissue ablation system, and more particularly to a combination microwave/radiofrequency ablation system for coagulating and resecting tissues.

2. Discussion of Related Art

Electrosurgical devices utilizing electromagnetic radiation have been developed for a variety of uses and applications. Typically, apparatus for use in ablation procedures include a power generation source, e.g., a microwave or radio frequency (RF) electrosurgical generator that functions as an energy source and a surgical instrument (e.g., microwave ablation probe having an antenna assembly) for directing energy to the target tissue. The generator and surgical instrument are typically operatively coupled by a cable assembly having a plurality of conductors for transmitting energy from the generator to the instrument, and for communicating control, feedback, and identification signals between the instrument and the generator.

There are several types of microwave probes in use, e.g., monopole, dipole, and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors that are linearly-aligned and positioned end-to-end relative to one another with an electrical insulator placed therebetween. Helical antenna assemblies include helically-shaped conductor configurations of various dimensions, e.g., diameter and length. The main modes of operation of a helical antenna assembly are normal mode (broadside), in which the field radiated by the helix is maximum in a perpendicular plane to the helix axis, and axial mode (end fire), in which maximum radiation is along the helix axis.

One use for a microwave probe is to dissect solid organs, such as liver or kidney, to remove entire diseased portions of the organ. During these procedures, it is important that blood loss from the dissected organ is minimized without compromising the efficacy of the procedure. It is also of particular importance to keep the procedure simple by reducing the number of surgical instruments used while also keeping the overall procedure time at a minimum.

Accordingly, it would be advantageous to provide one surgical instrument that performs a plurality of tasks during a tissue ablation procedure to effectively dissect a diseased portion of a solid organ.

SUMMARY

In one aspect of the present disclosure, a surgical instrument for ablating tissue is provided and includes a handle portion and a shaft assembly extending distally from the handle portion. The shaft assembly includes an outer shaft, a coaxial cable extending through the outer shaft, and an electrode coupled to a distal portion of the outer shaft. The coaxial cable has a distal portion disposed within the distal portion of the outer shaft. The distal portion of the coaxial cable forms a microwave antenna configured to transmit microwave energy radially outward and through the outer shaft. An actuation of the handle portion activates the transmission of the microwave energy from the microwave antenna or the transmission of the radiofrequency energy from the at least one electrode.

In some embodiments, the electrode may be disposed distally of the microwave antenna.

In some embodiments, the electrode may be disposed radially outward from the microwave antenna and out of alignment with the direction of travel of the microwave energy transmitted from the microwave antenna. The electrode may be a pair of bipolar electrodes.

In some embodiments, the distal portion of the outer shaft may have a wedge-shaped configuration.

In some embodiments, the shaft assembly may further include a reflector disposed within the distal portion of the outer shaft and about the microwave antenna.

In some embodiments, the reflector may have a semi-circular shape and be configured to direct the transmission of the microwave energy toward an edge of the outer shaft. The edge of the outer shaft may extend parallel with a longitudinal axis defined by the shaft assembly.

In some embodiments, the shaft assembly may further include a dielectric region disposed within the distal portion of the outer shaft.

In some embodiments, the reflector and a pair of adjoined lateral sides of the outer shaft may cooperatively define a cavity therein. The dielectric region may fill the cavity.

In some embodiments, the surgical instrument may further include a tube extending through the outer shaft and may be disposed radially outward from the microwave antenna. The tube may have a proximal portion configured to receive suction.

In some embodiments, the electrode may include a hooked distal portion disposed distally of the microwave antenna. The shaft assembly may further include an outer sheath disposed about the outer shaft and may be axially movable relative to the outer shaft between a first position, in which the hooked distal portion is disposed within the outer sheath, and a second position, in which the hooked distal portion is disposed distally of the outer sheath.

In another aspect of the present disclosure, a tissue ablation system is provided and includes a microwave generator configured to generate and transmit microwave energy, an electrosurgical generator configured to generate and transmit radiofrequency energy, and a surgical instrument. The surgical instrument includes a handle portion configured to be coupled to both of the microwave and electrosurgical generators, and a shaft assembly extending distally from the handle portion. The shaft assembly includes an outer shaft, a coaxial cable extending through the outer shaft, and an electrode coupled to a distal portion of the outer shaft. The coaxial cable has a proximal portion configured to be in electrical communication with the microwave generator, and a distal portion disposed within the distal portion of the outer shaft. The distal portion of the coaxial cable forms a microwave antenna configured to transmit the microwave energy radially outward and through the outer shaft. The electrode is coupled to the distal portion of the outer shaft and configured to be in electrical communication with the electrosurgical generator to transmit the radiofrequency energy. An actuation of the handle portion activates the transmission of the microwave energy from the microwave antenna or the transmission of the radiofrequency energy from the electrode.

In yet another aspect of the present disclosure, a method of resecting a portion of tissue is provided and includes positioning a microwave antenna of a surgical instrument adjacent a portion of tissue, transmitting microwave energy into the portion of the tissue, thereby precoagulating the portion of the tissue, deactivating the transmission of the microwave energy, and moving a distal portion of an outer shaft of the surgical instrument along the tissue while transmitting radiofrequency energy from an electrode of the surgical instrument into the tissue, thereby resecting the portion of the tissue.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Embodiments of the presently disclosed tissue ablation systems including various embodiments of a surgical instrument and methods of use thereof are described in detail with reference to the drawings, in which like reference numerals designate identical or corresponding elements in each of the several views. As used herein the term "distal" refers to that portion of the tissue ablation system or component thereof, that is closer to the patient, while the term "proximal" refers to that portion of the tissue ablation system or component thereof, that is farther from the patient.

As will be described in detail below, provided are embodiments of a surgical instrument of a tissue ablation system that switches between microwave energy transmission and radiofrequency energy transmission. For example, one embodiment of the disclosed surgical instruments includes a wedge-shaped outer shaft, a microwave antenna disposed within a distal portion of the outer shaft, and a monopolar electrode or bipolar electrodes disposed on the distal portion of the outer shaft. In operation, the microwave antenna is activated to transmit microwave energy out of an apex of the outer shaft and into tissue to precoagulate tissue. After the tissue is precoagulated, the microwave antenna is deactivated, and the electrode is activated to transmit radiofrequency energy into the tissue while moving the distal portion of the outer shaft along an outer surface of the tissue. The radiofrequency energy cuts or resects the precoagulated tissue to remove a portion of the tissue with minimal to no bleeding occurring.

As used herein, the term "pre-coagulate" means heating tissue to the extent necessary to prevent blood from flowing from the heated tissue upon resecting the tissue.

As used herein, "microwave" generally refers to electromagnetic waves in the frequency range of 300 megahertz (MHz) ($3 \times 10^8$ cycles/second) to 300 gigahertz (GHz) ($3 \times 10^{11}$ cycles/second).

As used herein, "tissue ablation" generally refers to any ablation procedure, such as, for example, microwave ablation, radiofrequency (RF) ablation, or microwave or RF ablation-assisted resection.

As used herein, "transmission line" generally refers to any transmission medium that can be used for the propagation of signals from one point to another.

As used herein, "fluid" generally refers to a liquid, a gas or both.

As used herein, "controller" generally refers to any electrical device that employs digital and/or analog components to generate digital and/or analog signals to control or drive another device. The term "controller" may refer to a digital signal processor, a microcontroller, or a computer having a processor, a memory, and input/output ports for carrying out some of the methods described herein.

Various embodiments of the presently disclosed surgical instruments are suitable for tissue ablation and for use to pre-coagulate tissue for microwave ablation-assisted surgical resection. Although various methods described herein below are targeted toward microwave ablation and the destruction and/or resection of targeted tissue, methods for directing electromagnetic radiation may be used with other therapies in which the target tissue is partially destroyed, damaged, or dissected. In addition, the teachings of the present disclosure may apply to a dipole, monopole, helical, or other suitable type of microwave antenna.

Figure 1:
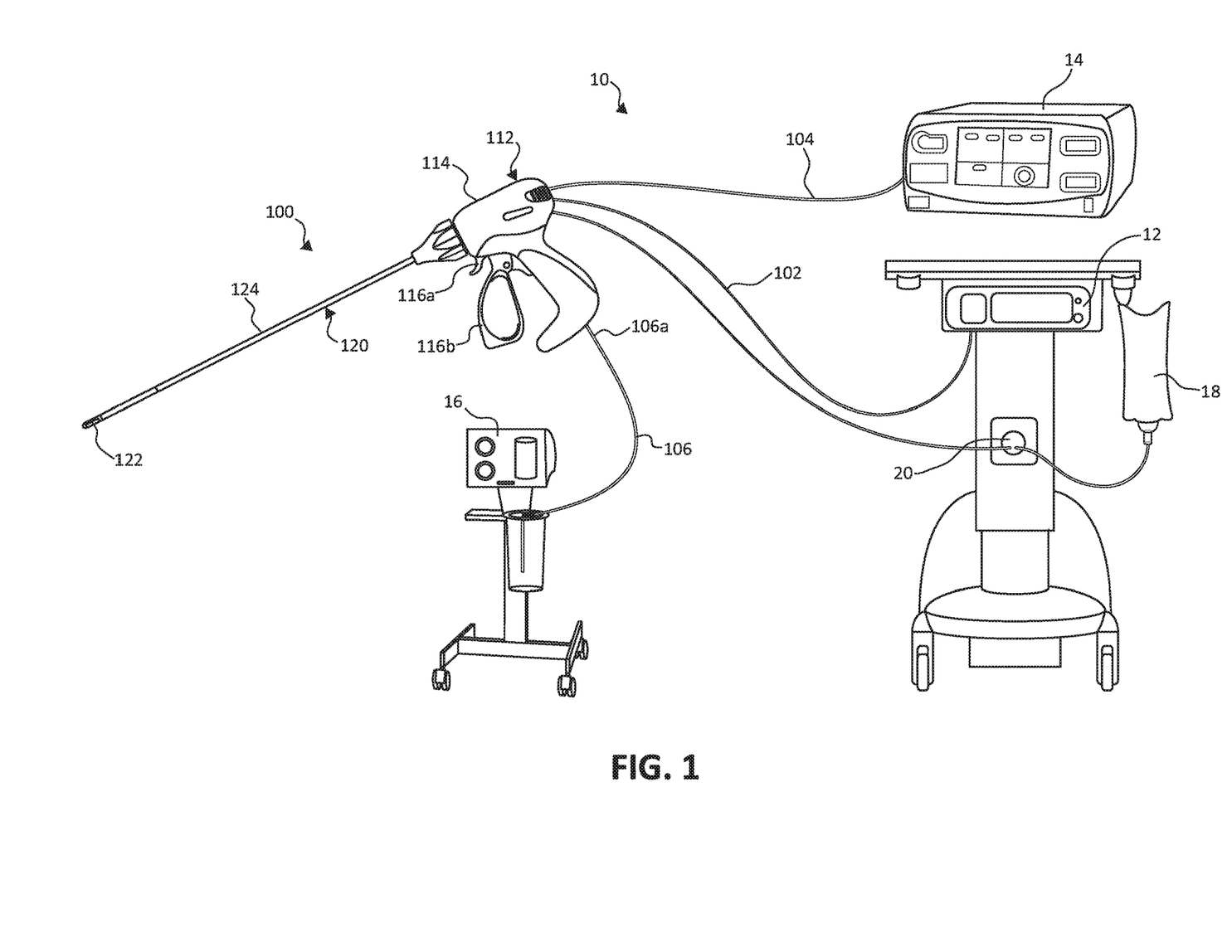
FIG. 1 is perspective view of a tissue ablation system including a surgical instrument, an electrosurgical generator, a microwave generator, and a surgical suction pump in accordance with the principles of the present disclosure.

With reference to FIG. 1, a dual microwave/RF energy ablation and cutting system 10 is illustrated and generally includes a tissue ablation instrument 100 operably coupled to a microwave generator 12, an electrosurgical generator 14, and a surgical suction pump 16. The microwave generator 12 generates a microwave energy signal that is transmitted to a radiating section "R" (FIG. 2) of the surgical instrument 100 via a coaxial cable 102. The microwave energy generated by the microwave generator 12 may be in the range of about 915 MHz to about 25.0 GHz. In some embodiments, the microwave generator 12 may operate at 915 MHz, 2450 MHz, and/or 5800 Mhz. The electrosurgical generator 14 generates a radiofrequency signal and outputs it to bipolar electrodes 142a, 142b (FIG. 3B) of the surgical instrument 100 via a transmission line 104. The surgical suction pump 16 produces suction and applies the suction to a port 140 (FIG. 2) located a distal portion of the surgical instrument 100 via a suction tube 106. In some embodiments, the tissue ablation system 10 may further include a source of coolant 18 (e.g., saline) and a pump 20 for conveying the coolant to the surgical instrument 100 to cool various components therein during operation.

The surgical instrument 100 of the tissue ablation system 10 includes a handle portion 112 and a shaft assembly 120 extending distally from the handle portion 112. The handle portion 112 has a body portion 114 through which each of the coaxial cable 102, the transmission line 104, and the suction tube 106 extend. The handle portion 112 includes first and second controls 116a, 116b such as buttons, switches, or triggers, movably coupled to the body portion 114 of the handle portion 112. The first control 116a may be in electrical communication (e.g., wirelessly or wired connection) with the microwave generator 12 and configured to selectively actuate a microwave function of the surgical instrument 100, and the second control 116b may be in electrical communication (e.g., wirelessly or wired connection) with the electrosurgical generator 14 and configured to selectively actuate a radiofrequency function of the surgical instrument 100. In some embodiments, an actuation of the microwave function and/or the radiofrequency function of the surgical instrument 100 may be accomplished via a button or a footswitch external to the surgical instrument 100.

With reference to FIGS. 1, 2, 3A, and 3B, the shaft assembly 120 of the surgical instrument 100 includes a hollow, elongated body or outer shaft 122 and an outer coating or sheath 124 covering an outer surface of the outer shaft 122. The outer shaft 122 has a proximal portion 122a coupled to the handle portion 112 and a distal portion 122b. The outer shaft 122 defines a longitudinal axis "X" and has a wedge-shaped or triangular cross-sectional profile. The outer shaft 122 has a planar base 126a and a pair sides 126b, 126c extending at acute angles downwardly from the base 126a. The sides 126b, 126c of the outer shaft 122 form an acuminate apex or edge 128 at the point at which they are adjoined. The edge 128 of the outer shaft 122 extends parallel with and along the longitudinal axis "X" thereof and is configured to contact and move along a tissue surface, as will be described. In some embodiments, the outer shaft 122 may assume any suitable cross-sectional configuration, such as, for example, circular, V-shaped, U-shaped, oval, square, and/or polygonal.

Figure 2:
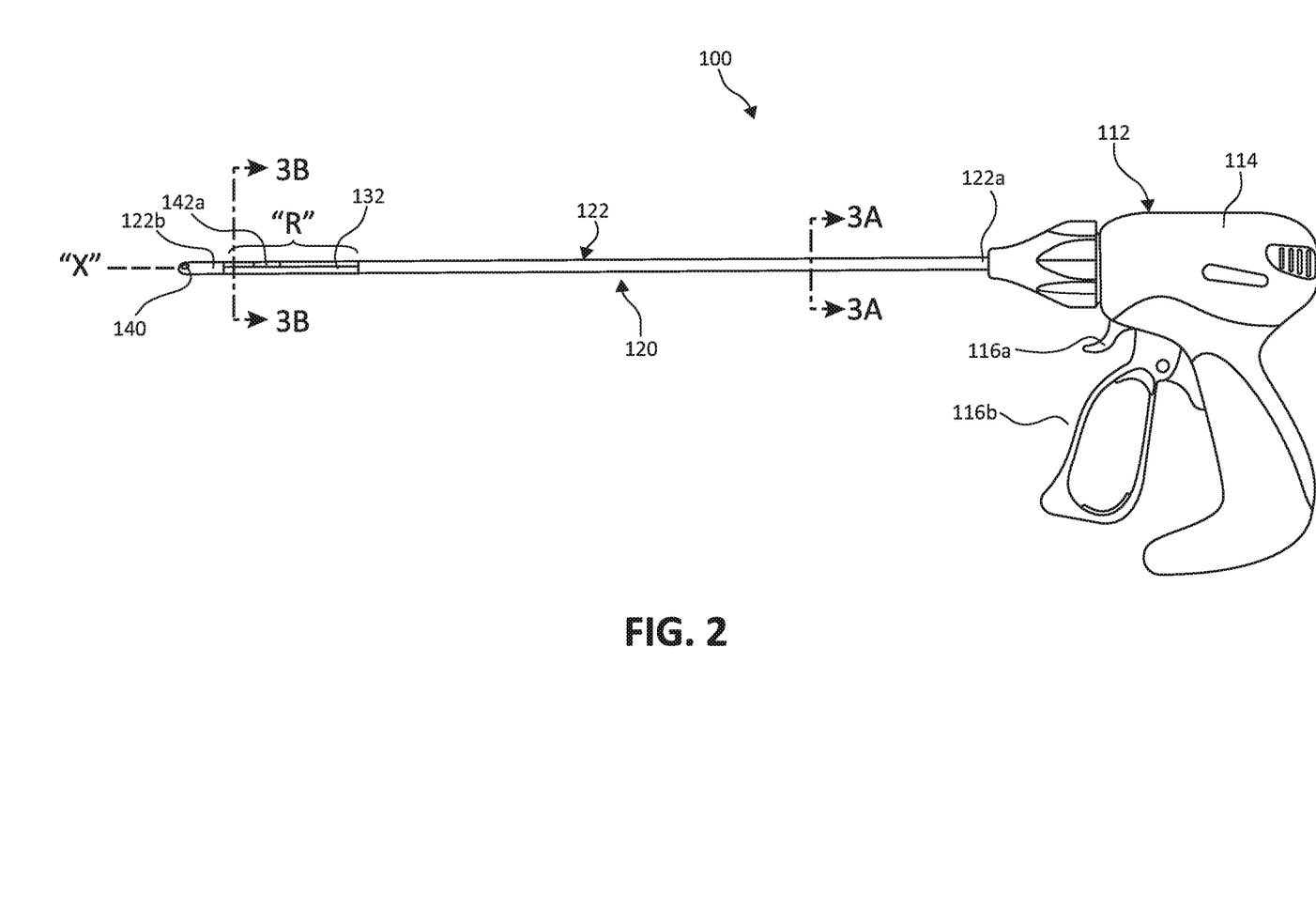
FIG. 2 is a side view of the surgical instrument of FIG. 1, illustrating a microwave antenna disposed at a distal portion of a shaft assembly.
Figure 5:
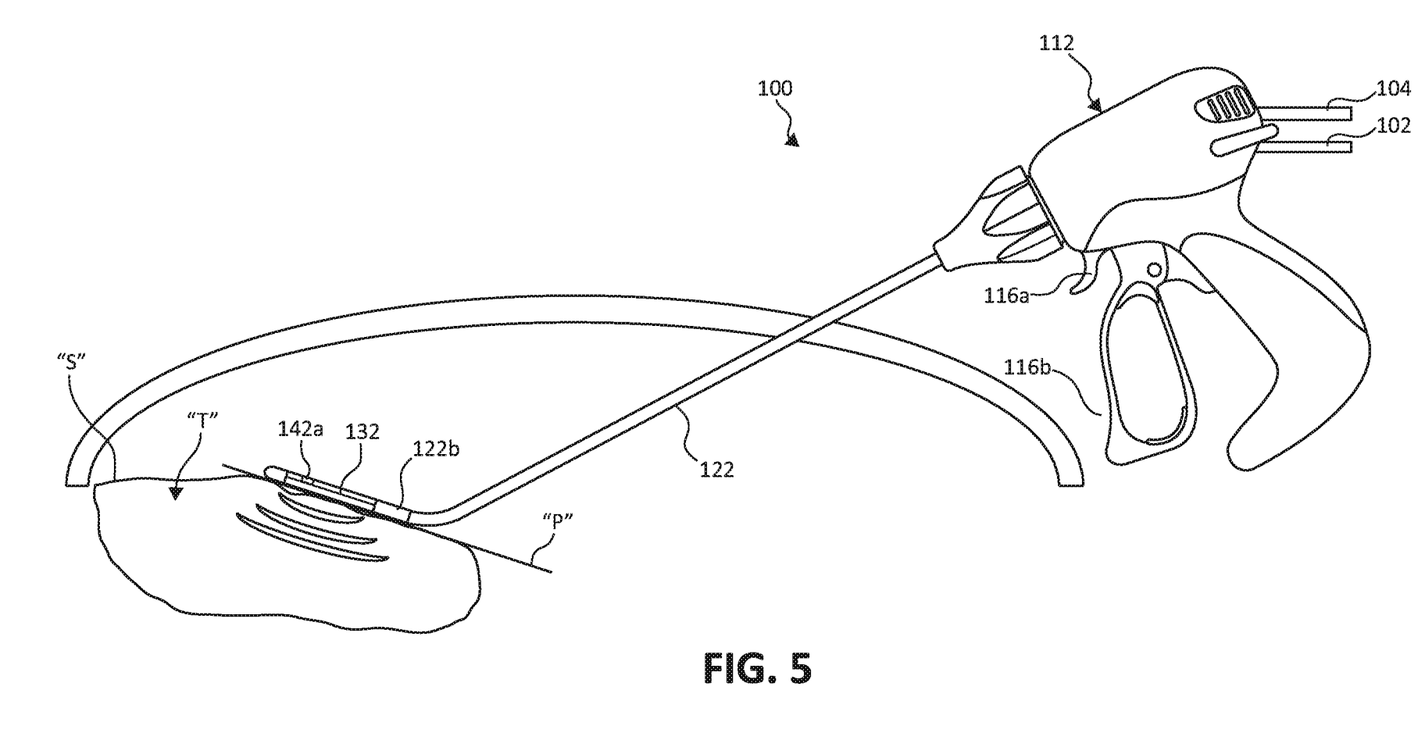
FIG. 5 is a perspective view of the surgical instrument of FIG. 4, illustrating an exemplary ablation procedure.

The distal portion 122b of the outer shaft 122 may be configured to articulate relative to the proximal portion 122a thereof. In particular, the distal portion 122b of the outer shaft 122 may move relative to the proximal portion 122a between a non-articulated configuration as shown in FIG. 2, in which the distal portion 122b is coaxial with the longitudinal axis "X" of the outer shaft 122, and an articulated position as shown in FIG. 5, in which the distal portion 122b extends at a non-zero angle relative to the longitudinal axis "X" of the outer shaft 122. It is contemplated that the distal portion 122b of the outer shaft 122 may be resiliently biased toward the non-articulated position via a biasing member (not shown) or a shape-memory alloy, and may be articulated by applying external pressure on the distal portion 122b. Alternatively, articulation wires and articulated segments may be employed to achieve the depicted articulation as is common in the surgical arts.

Figure 3A:
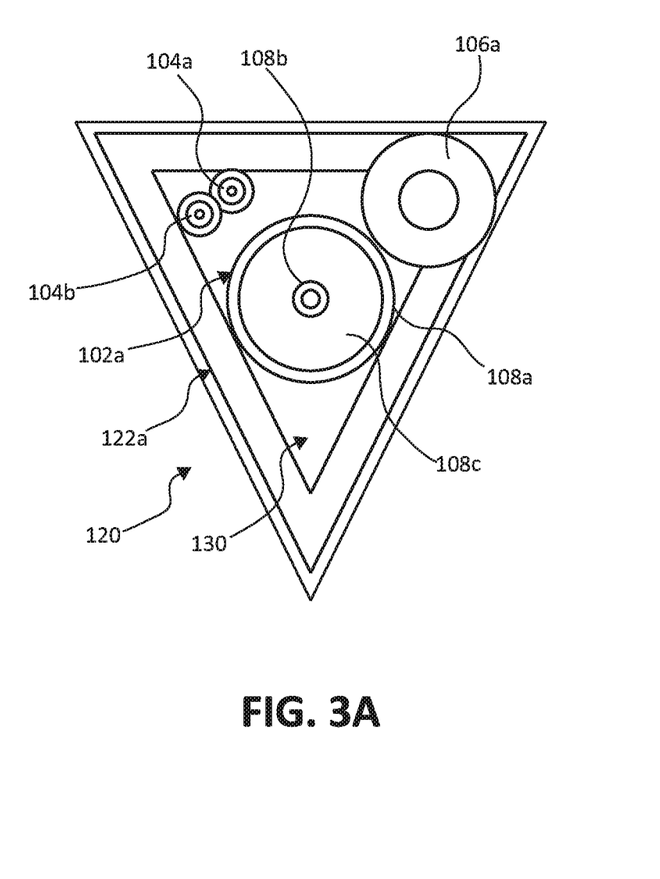
FIG. 3A is a cross-section, taken along line 3A-3A of FIG. 2, of a proximal portion of the shaft assembly.
Figure 3B:
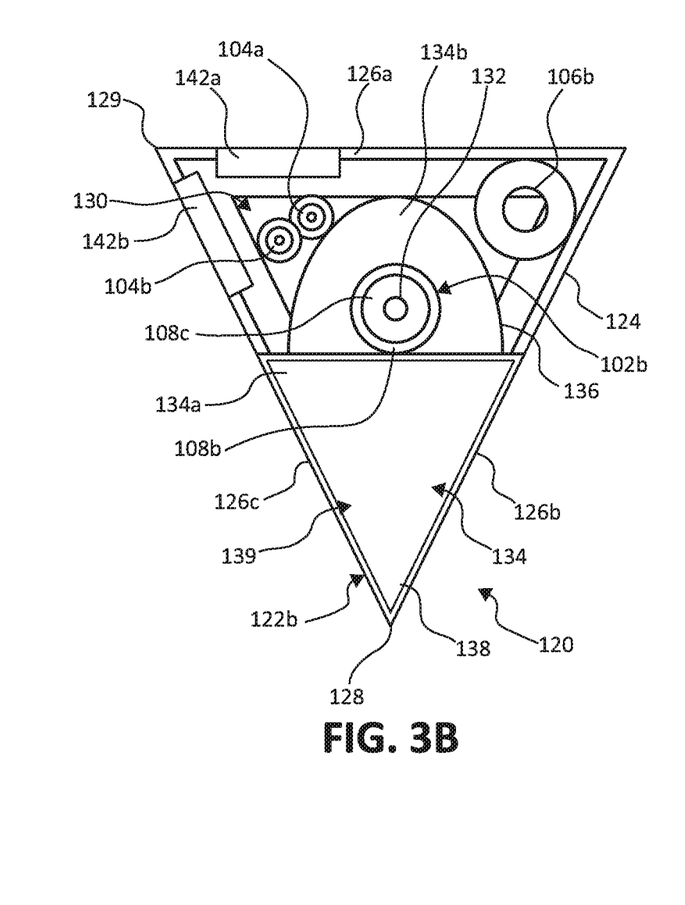
FIG. 3B is a cross-section, taken along line 3B-3B of FIG. 2, of a distal portion of the shaft assembly.

With reference to FIGS. 3A and 3B, the coaxial cable 102 of the surgical instrument 100 extends axially through a channel 130 defined through the outer shaft 122 and has a proximal portion 102a disposed with the proximal portion 122a of the outer shaft 122 and a distal portion 102b disposed within the distal portion 122b of the outer shaft 122. The proximal portion 102a of the coaxial cable 102 has a larger diameter, e.g., 1.5×-3× the diameter of the distal portion 102a, such that the proximal portion 102a is well-suited for dissipating heat therefrom during the transmission of microwave energy therethrough. The coaxial cable 102 has an outer conductor 108a, an inner conductor 108b extending coaxially through the outer conductor 108a, and a dielectric 108c disposed between the inner and outer conductors 108a, 108b. The inner conductor 108b extends distally beyond a distal end of the outer conductor 108a to form or define the microwave antenna 132, from which microwave energy originating from the microwave generator 12 is emitted radially outward.

The shaft assembly 120 of the surgical instrument 100 may further include a solid core dielectric region 134 disposed within the distal portion 122b of the outer shaft 122, and a reflector 136 disposed about an upper portion 134b of the dielectric region 134 and about the microwave antenna 132. The dielectric region 134 has a bottom portion 134a received between the two lateral sides 126b, 126c of the outer shaft 122, and an upper portion 134b. The lower portion 134a of the dielectric region 134 has a generally triangular configuration and the upper portion 134b has a generally semicircular configuration. The lower portion 134a includes a bottom acuminate edge 138 through which microwave energy is transmitted. The bottom edge 138 of the lower portion 134a is disposed adjacent the edge 128 of the outer shaft 122 and is exposed (i.e., not covered by the reflector 136). The upper portion 134b of the dielectric region 134 has the distal portion 102b of the coaxial cable 102 extending therethrough.

The dielectric region 134 may be formed from any suitable dielectric material having low-loss dielectric loading properties that possesses sufficient mechanical and biocompatible properties to withstand conditions associated with surgical procedures, including without limitation ceramic material; PTFE; Teflon®; or Ultem™ amorphous thermoplastic polyetherimide (PEI) resin distributed by SABIC Innovative Plastics of Pittsfield, Mass., USA.

The reflector 136 of the shaft assembly 120 surrounds the upper portion 134b of the dielectric region 134 and has a semi-circular shape, which facilitates directing or focusing microwave energy toward the edge 128 of the outer shaft 122. In some embodiments, the reflector 136 may assume any suitable shape for focusing microwave energy through the dielectric region 134 and toward the edge 128 of the outer shaft 122, such as, for example, parabolic, semi-hemispherical, or the like. It is contemplated that the reflector 136 and the pair of lateral sides 126b, 126c of the outer shaft 122 cooperatively define a cavity 139 therein, which is filled by the dielectric region 134. The reflector 136 may be a layer or coating and may be formed from any suitable material having the capability to reflect microwave energy, such as, without limitation, copper plating, copper foil, or Polyflon™ electroplated PTFE.

With reference to FIGS. 2, 3A, and 3B, the suction tube 106 of the surgical instrument 100 extends axially through the outer shaft 122. The tube 106 has a proximal portion 106a coupled to the surgical suction pump 16 and a distal portion 106b disposed radially outward from the microwave antenna 132 and out of the pathway of microwave energy transmitted from the microwave antenna 132. The distal portion 106b of the tube 106 extends distally beyond the microwave antenna 132 and terminates adjacent a distal tip of the outer shaft 122. The outer shaft 122 and the outer sheath 124 define a port 140 therethrough that is fluidly coupled to the distal portion 106b of the tube 106 such that the port 140 acts as a suction port when the surgical suction pump 16 is activated.

With reference to FIGS. 3A and 3B, the shaft assembly 120 of the surgical instrument 100 further includes a pair of bipolar electrodes 142a, 142b disposed within the distal portion 122b of the outer shaft 122 and radially outward from the microwave antenna 132. The location of the electrodes 142a, 142b is selected so as to position the electrodes 142a, 142b out of alignment with the pathway of the microwave energy transmitted from the microwave antenna 132. The electrodes 142a, 142b are electrically coupled to the electrosurgical generator 14 via the transmission line 104. The transmission line 104 splits into two electrode leads 104a, 104b in the outer shaft 122. A first electrode 142a of the pair of bipolar electrodes may be disposed on the base 126a of the outer shaft 122, and a second electrode 142b of the pair of bipolar electrodes may be disposed on the second lateral side 126c of the outer shaft 122, such that the first and second electrodes 142a, 142b are angled relative to one another. The first and second electrodes 142a, 142b are in close proximity to one another (e.g., within about 0.025 and 0.050 inches from one another) while remaining electrically insulated along their length.

Figure 4:
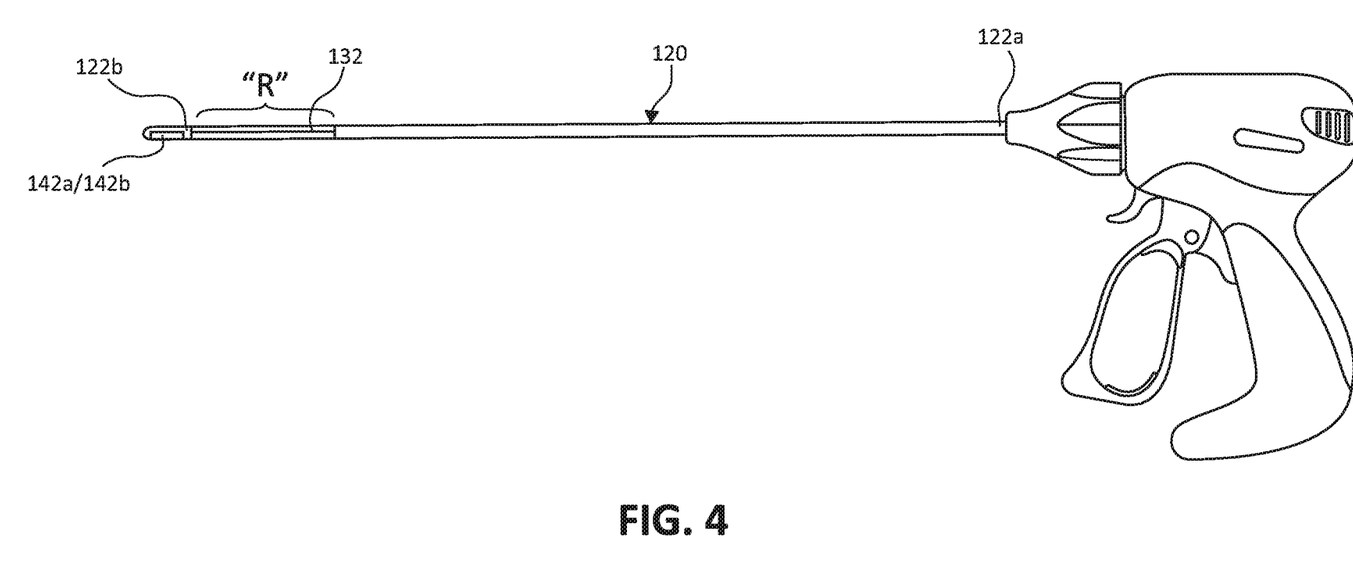
FIG. 4 is a side view of another embodiment of a shaft assembly having bipolar electrodes disposed distally of a microwave antenna.

As illustrated in the embodiment of FIG. 4, instead of positioning the bipolar electrodes 142a, 142b radially outward from the microwave antenna 132, the bipolar electrodes 142a, 142b may be disposed distally of the microwave antenna 132. In this way, the microwave energy transmitted from the microwave antenna 132, which is directed perpendicularly relative to the longitudinal axis "X" of the outer shaft 122, will not travel through the distally-located electrodes 142a, 142b.

In operation, as shown in FIG. 5, a portion of tissue, such as a section of liver tissue "T" may be ablated and resected using the tissue ablation system 10 of the present disclosure. The edge 128 of the distal portion 122b of the outer shaft 122 may be placed in contact with a surface "S" of the liver tissue "T" to be resected. Due to the acuminate design of the edge 128 of the outer shaft 122, contacting the edge 128 of the outer shaft 122 with the tissue surface "S" forms a depression or valley in the tissue "T." With the edge 128 of the outer shaft 122 engaged with the tissue "T," the first control 116a of the handle portion 112 is actuated to activate the microwave function of the surgical instrument 100, whereby the microwave generator 12 transmits microwave energy to the microwave antenna 132 via the coaxial cable 102.

The reflector 136 of the shaft assembly 120 redirects a portion of the microwave energy towards the edge 138 of the dielectric region 134, the edge 128 of the outer shaft 122, and ultimately into the valley of the tissue "T." As the microwave energy is transmitted into the valley of the tissue "T," the surgical instrument 100 is manipulated to move or slide the edge 128 of the outer shaft 122 along a resection plane "P" of the liver tissue "T," thereby pre-coagulating the underlying tissue at a depth proportional to the frequency of the microwave energy and the length of time the microwave antenna 132 is activated.

Movement of the edge 128 of the outer shaft 122 of the surgical instrument 100 along the resection plane "P" is continued until a desired depth and/or width of pre-coagulation is achieved. Upon achieving the desired depth and width of tissue pre-coagulation, transmission of the microwave energy is deactivated and the bipolar electrodes 142a, 142b are placed adjacent the tissue surface "S" of the pre-coagulated tissue "T."

As shown in FIG. 3A in conjunction with FIG. 2, to orient the bipolar electrodes 142a, 142b adjacent the tissue surface "S," (FIG. 5) the outer shaft 122 of the surgical instrument 100 is rotated about the longitudinal axis "X" from approximately 5°- to approximately 180°, and in some embodiments approximately 130°, to engage a second edge 129 (FIG. 3B) of the outer shaft 122 with the tissue surface "S" (FIG. 5). The second edge 129 is defined by the second lateral side 126c of the outer shaft 122 and the base 126a of the outer shaft 122. In the embodiment illustrated in FIG. 4, to orient the bipolar electrodes 142a, 142b adjacent the tissue surface "S," the outer shaft 122 of the surgical instrument 100 is tilted toward the distal tip of the outer shaft 122 rather than be rotated about the longitudinal axis "X."

While moving the second edge 129 of the outer shaft 122 along the resection plane "P," the second control 116b is actuated to activate the radiofrequency function of the surgical instrument, whereby the electrosurgical generator 14 transmits radiofrequency energy to the bipolar electrodes 142a, 142b via the electrode leads 104a, 104b. The radiofrequency energy is directed out of the second edge 129 of the outer shaft 122 to resect the liver tissue "T" along the resection plane "P."

The above-noted steps may be repeated to pre-coagulate the tissue "T" at increasingly greater depths, and then resect along the pre-coagulation line until a desired portion of the tissue "T" is separated from the remainder of the organ. The surgical suction pump 16 may be activated at any point during and/or after the procedure to remove surgical debris and/or surgical smoke via the port 140 of the surgical instrument 100. By pre-coagulating the tissue using microwave energy, blood loss is minimized since the resection line for the bi-polar resection or cutting is within the boundaries of the pre-coagulated tissue. Further, this procedure reduces the opportunities for reseeding of cancerous tissue by this same pre-coagulation process prior to any resection or cutting of the organ.

With reference to FIGS. 6-9, another embodiment of a dual microwave/RF energy ablation system is illustrated as system 210, which is similar to the tissue ablation system 10 described above with reference to FIGS. 1-5. Due to the similarity between the tissue ablation systems 10, 210 of the present disclosure, only those details viewed as important in elucidating selected differences between the two ablation systems 10, 210 will be described in detail.

Figure 6:
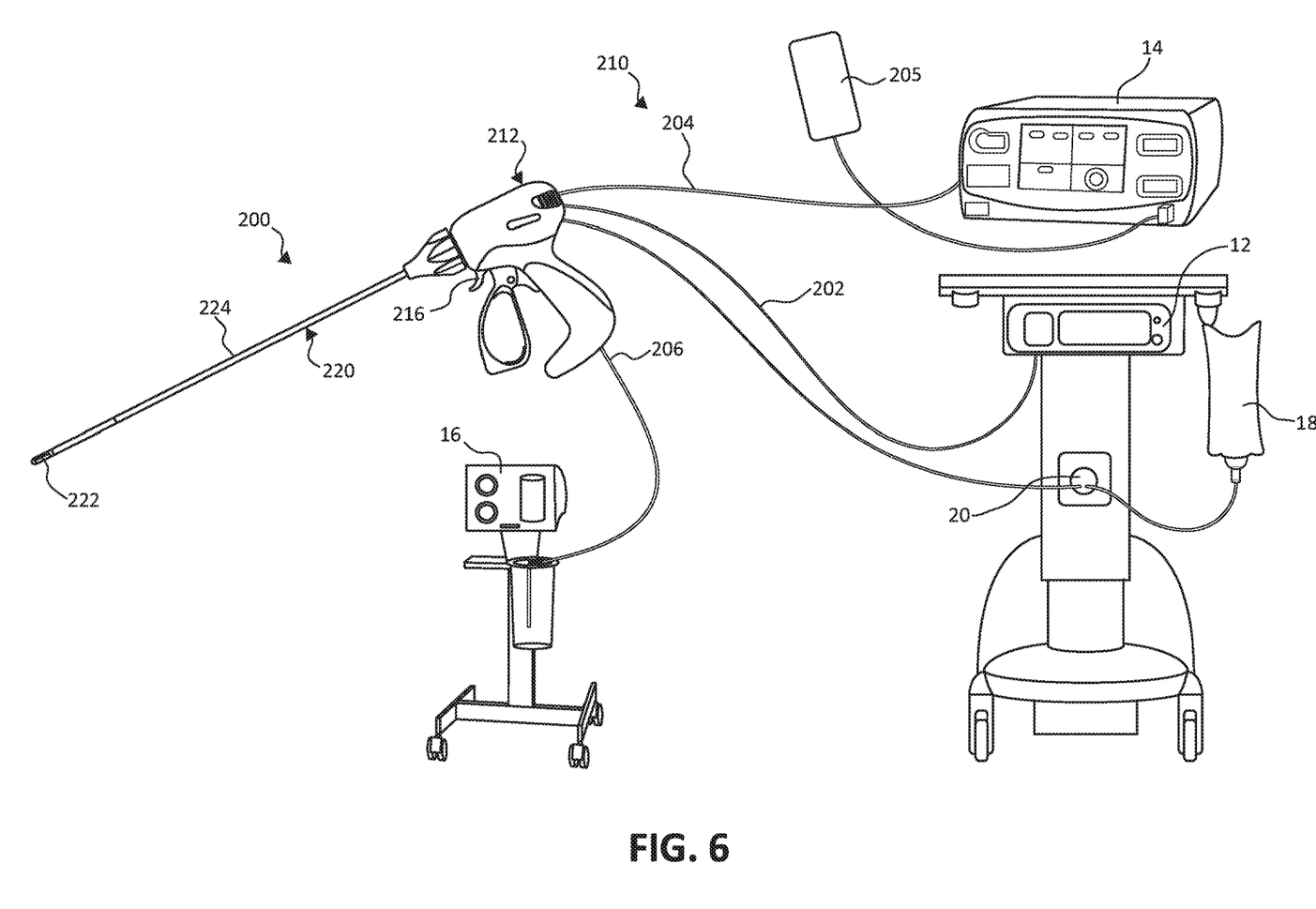
FIG. 6 is a perspective view of another embodiment of a tissue ablation system including a surgical instrument, an electrosurgical generator, a microwave generator, and a surgical suction pump in accordance with the principles of the present disclosure.

The dual microwave/RF energy ablation system 210 generally includes a tissue ablation instrument 200 operably coupled to the microwave generator 12, the radiofrequency generator 14, and the surgical suction pump 16. The microwave generator 12 generates a microwave signal and outputs it to a microwave antenna 232 of the surgical instrument 200 via a coaxial cable 202. The electrosurgical generator 14 generates a radiofrequency signal and outputs it to a monopolar electrode 242 of the surgical instrument 200 via a transmission line 204. A return signal, originating from the transmission line 204, may be received by a ground pad 205 coupled to the electrosurgical generator 14. The surgical suction pump 16 produces suction and applies the suction to a port 240 located a distal portion of the surgical instrument 200 via a suction tube 206. In some embodiments, the tissue ablation system 210 may further include a coolant 18 (e.g., saline) and a pump 20 for conveying the coolant to the surgical instrument 200 to cool various components therein during operation.

Figure 7:
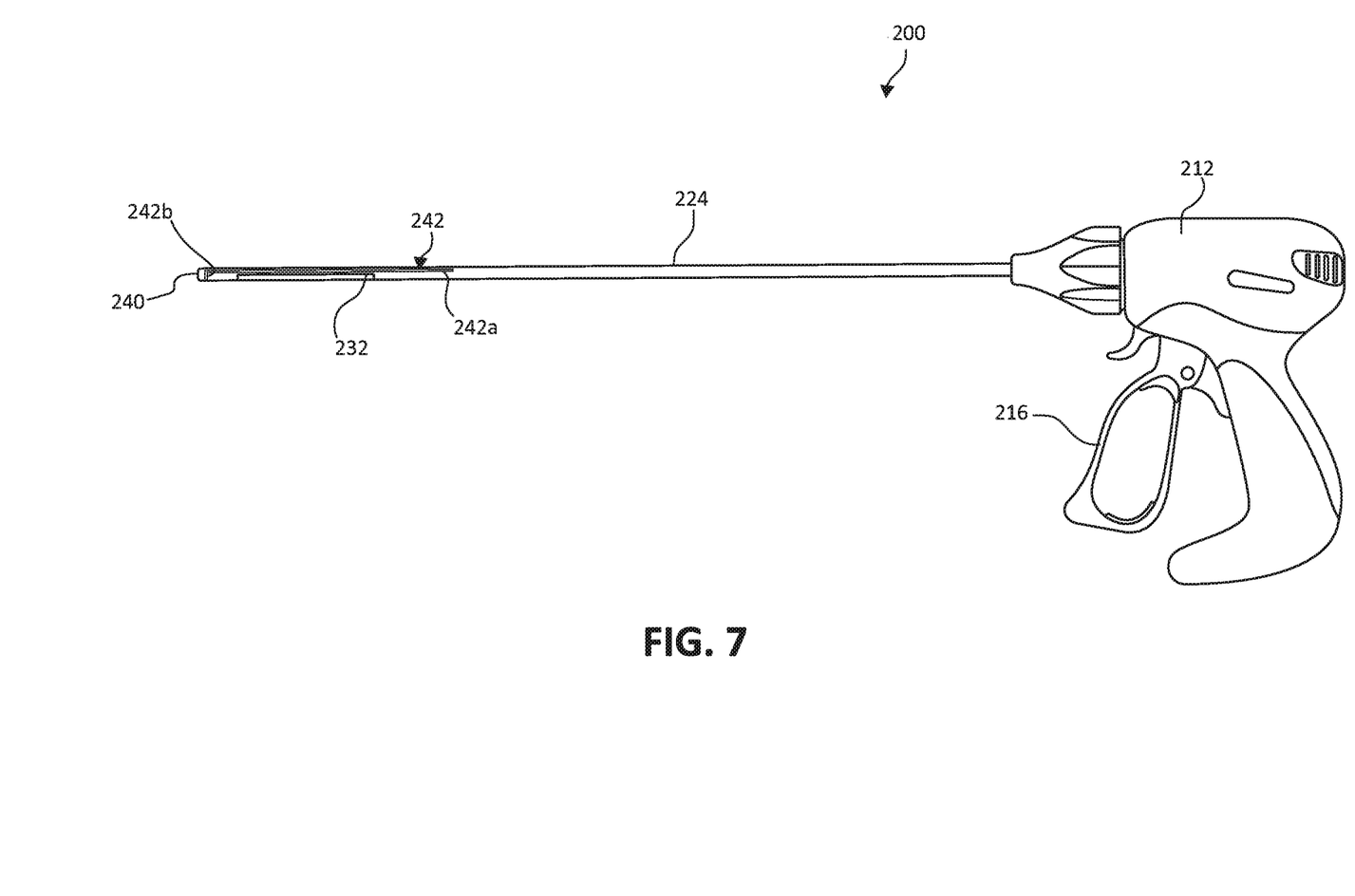
FIG. 7 is a side view of the surgical instrument of FIG. 6, illustrating an outer sheath covering a monopolar electrode.
Figure 8:
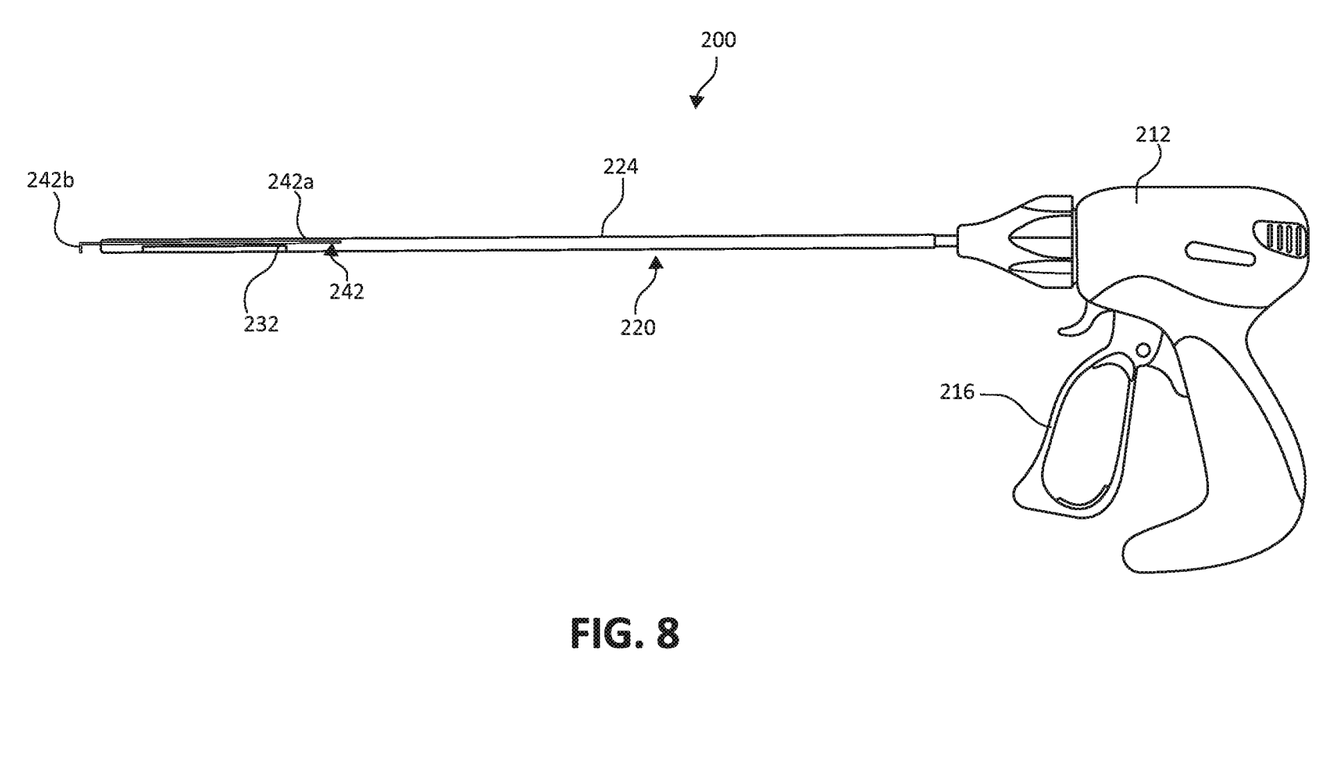
FIG. 8 is a side view of the surgical instrument of FIG. 6, illustrating the monopolar electrode disposed outside of the outer sheath.

The surgical instrument 200 of the tissue ablation system 210 includes a handle portion 212 and a shaft assembly 220 extending distally from the handle portion 212. The shaft assembly 220 includes a hollow, elongated body or outer shaft 222 and an outer coating or sheath 224 covering an outer surface of the outer shaft 222. The outer sheath 224 is operably coupled to a control 216, such as a button, switch, or trigger, of the handle portion 212. The outer sheath 224, in response to an actuation of the control 216, axially moves relative to the handle portion 212 and the outer shaft 222 between a proximal position and a distal position to selectively expose a hook-shaped monopolar electrode 242 of the surgical instrument 200, as will be described in detail below.

The shaft assembly 220 further includes a coaxial cable 202 that forms the microwave antenna 232 at its terminal end. The microwave antenna 232 and its associated components (e.g., a reflector and dielectric region) are similar to the microwave antenna 132 described above, and will therefore not be described in further detail herein. The monopolar electrode 242 is disposed between an outer surface of the outer shaft 222 and an inner surface of the outer sheath 224, and is electrically coupled to the electrosurgical generator 14. The monopolar electrode 242 has a proximal portion 242a in communication with the transmission line 204, and a distal portion 242b extending distally beyond the microwave antenna 232. In some embodiments, the proximal portion 242a of the monopolar electrode 242 may be mechanically coupled to the control 216 such that an actuation of the control 216 moves the monopolar electrode 242 between proximal and distal positions relative to the outer sheath 224.

The distal portion 242b of the monopolar electrode 242 may have a hooked configuration for depressing tissue upon contact therewith. In particular, the distal portion 242b extends at a perpendicular angle relative to the longitudinal axis defined by the outer shaft 222. In some embodiments, the distal portion 242b of the monopolar electrode 242 may extend at a variety of angles relative to the longitudinal axis of the outer shaft 222, e.g., 0° to 180°. In other embodiments, rather than the distal portion 242b of the monopolar electrode 242 assuming a hooked configuration, the distal portion 242b may assume a helical configuration, a curved configuration, or the like.

Figure 9:
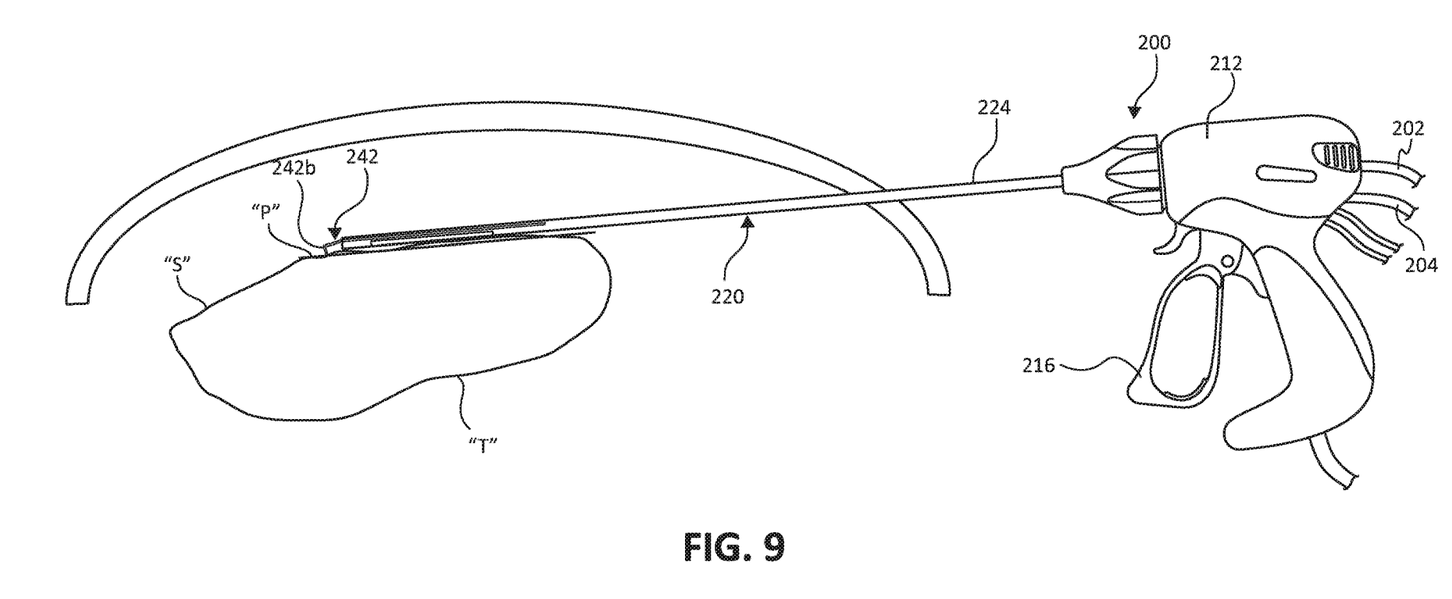
FIG. 9 is a perspective view of the surgical instrument of FIG. 6, illustrating an exemplary ablation procedure.

In operation, as shown in FIG. 9, a portion of tissue, such as a section of liver tissue "T" may be ablated and resected using the tissue ablation system 210 of the present disclosure. With the outer sheath 224 of the surgical instrument 200 covering the distal portion 242b of the monopolar electrode 242b, an edge of the distal portion of the outer shaft 222 may be placed in contact with a surface "S" of the liver tissue "T" to be resected. Contacting the edge of the outer shaft 222 with the tissue surface "S" forms a depression or valley in the tissue "T." The handle portion 212 is actuated to activate the microwave function of the surgical instrument 200, whereby the microwave generator 12 transmits microwave energy to the microwave antenna 232 via the coaxial cable 202.

The microwave antenna 232 directs the microwave energy radially outward therefrom and toward the edge of the outer shaft 222 and into the valley formed in the tissue "T." As the microwave energy is transmitted into the valley of the tissue "T," the surgical instrument 200 is manipulated to move or slide the edge of the outer shaft 222 along a resection plane "P" of the liver tissue "T," thereby pre-coagulating the underlying tissue at a depth proportional to the frequency of the microwave energy and the length of time the microwave antenna 232 is activated.

Movement of the edge of the outer shaft 222 of the surgical instrument 200 along the resection plane "P" is continued until a desired depth and/or width of tissue pre-coagulation is achieved. Upon achieving the desired depth and width of tissue pre-coagulation, transmission of the microwave energy is deactivated and the outer sheath 224 of the shaft assembly 220 is moved proximally toward the proximal position to expose the distal portion 242b of the monopolar electrode 242. In some embodiments, instead of moving the outer sheath 242 proximally to expose the monopolar electrode distal portion 242b, the monopolar electrode 242 may be moved distally beyond the outer sheath 224. With the distal portion 242b of the monopolar electrode 242 exposed, the distal portion 242b of the monopolar electrode 242 contacts the tissue surface "S" of the pre-coagulated tissue along the resection plane "P."

While moving the monopolar electrode 242 along the resection plane "P," the control 216 of the handle portion 212 is actuated to activate the radiofrequency function of the surgical instrument 200, whereby the electrosurgical generator 14 transmits radiofrequency energy to the monopolar electrode 242, whereby the radiofrequency energy is directed into the liver tissue "T" to resect the liver tissue "T" along the resection plane "P."

The above-noted steps may be repeated to pre-coagulate the tissue "T" at increasingly greater depths until the desired volume of the tissue "T" is pre-coagulated and resected from the remainder of the organ. The surgical suction pump 16 may be activated at any point during and/or after the procedure to remove surgical debris and/or surgical smoke via the port 240 of the surgical instrument 200.

The above-described tissue ablation systems are capable of directing microwave and radiofrequency energy into tissue, and may be suitable for use in a variety of procedures and operations. The above-described tissue ablation systems may be suitable for utilization with hand-assisted, endoscopic, and laparoscopic surgical procedures. The above-described tissue ablation systems may also be suitable for utilization in open surgical applications.

An effective method of identifying cancerous or diseased target tissue involves the use of a computed tomographic (CT) image. The use of CT as a diagnostic tool has now become routine and CT results are now frequently the primary source of information available to the practitioner regarding the size and location of a lesion. This information is used by the practitioner in planning an operative procedure such as a biopsy, but is only available as "offline" information which must typically be memorized to the best of the practitioner's ability prior to beginning a procedure. In addition to inputting target information, integration with the CT data provides improved system functionality, thereby greatly facilitating the planning of a pathway to an identified target as well as providing the ability to navigate through the body to the target location.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A surgical instrument for ablating tissue, comprising:
a handle portion; and
a shaft assembly extending distally from the handle portion and including:
an outer shaft having a distal portion;
a coaxial cable extending through the outer shaft and having a distal portion disposed within the distal portion of the outer shaft, the distal portion of the coaxial cable forming a microwave antenna configured to transmit microwave energy radially outward and through a first apex of the outer shaft; and
at least one electrode coupled to the distal portion of the outer shaft and disposed closer to a second apex defined by the outer shaft than the first apex, the at least one electrode configured to transmit radiofrequency energy, wherein an actuation of the surgical instrument activates at least one of the transmission of the microwave energy from the microwave antenna or the transmission of the radiofrequency energy from the at least one electrode.

2. The surgical instrument according to claim 1, wherein the at least one electrode is disposed distally of the microwave antenna.

3. The surgical instrument according to claim 1, wherein the at least one electrode is disposed radially outward from the microwave antenna and out of alignment with the direction of travel of the microwave energy being transmitted from the microwave antenna.

4. The surgical instrument according to claim 1, wherein the at least one electrode is a pair of bipolar electrodes.

5. The surgical instrument according to claim 1, wherein the distal portion of the outer shaft has a wedge-shaped configuration.

6. The surgical instrument according to claim 5, wherein the shaft assembly further includes a reflector disposed within the distal portion of the outer shaft and about the microwave antenna.

7. The surgical instrument according to claim 6, wherein the reflector has a semi-circular shape and is configured to direct the transmission of the microwave energy toward the first apex of the outer shaft, the first apex of the outer shaft extending parallel with a longitudinal axis defined by the shaft assembly.

8. The surgical instrument according to claim 7, wherein the shaft assembly further includes a dielectric region disposed within the distal portion of the outer shaft.

9. The surgical instrument according to claim 8, wherein the reflector and a pair of adjoined lateral sides of the outer shaft cooperatively define a cavity therein, the dielectric region filling the cavity.

10. The surgical instrument according to claim 1, wherein the at least one electrode is disposed on a lateral side of the outer shaft.

11. A tissue ablation system, comprising:
a microwave generator configured to generate and transmit microwave energy;
an electrosurgical generator configured to generate and transmit radiofrequency energy; and
a surgical instrument including:
a handle portion configured to be coupled to both of the microwave and electrosurgical generators; and
a shaft assembly extending distally from the handle portion and including:
an outer shaft having a distal portion;
a coaxial cable extending through the outer shaft and having a proximal portion configured to be in electrical communication with the microwave generator, and a distal portion disposed within the distal portion of the outer shaft, the distal portion of the coaxial cable forming a microwave antenna configured to transmit the microwave energy radially outward and through the outer shaft;
at least one electrode coupled to the distal portion of the outer shaft and configured to be in electrical communication with the electrosurgical generator to transmit the radiofrequency energy, wherein an actuation of the surgical instrument activates at least one of the transmission of the microwave energy from the microwave antenna or the transmission of the radiofrequency energy from the at least one electrode; and
a reflector disposed within the distal portion of the outer shaft and about the microwave antenna, wherein the reflector is configured to direct the microwave energy from the microwave antenna toward a first apex defined by the outer shaft, the at least one electrode being disposed closer to a second apex defined by the outer shaft than the first apex.

12. The tissue ablation system according to claim 11, wherein the distal portion of the outer shaft has a wedge-shaped configuration.

13. The tissue ablation system according to claim 12, wherein the reflector has a semi-circular shape, the first apex of the outer shaft extending parallel with a longitudinal axis defined by the shaft assembly.

14. The tissue ablation system according to claim 13, wherein the shaft assembly further includes a dielectric region filling a cavity cooperatively defined by the reflector and a pair of adjoined lateral sides of the outer shaft.

15. The tissue ablation system according to claim 11, wherein the shaft assembly further includes an outer sheath disposed about the outer shaft, the at least one electrode including a hooked distal portion disposed distally of the microwave antenna and within the outer sheath.

16. The tissue ablation system according to claim 11, wherein the outer shaft has a wedge-shaped configuration, the at least one electrode including a pair of bipolar electrodes disposed on a respective pair of adjoined, lateral sides of the outer shaft.

17. A method of resecting a portion of tissue, comprising:
positioning a microwave antenna of a surgical instrument adjacent a portion of tissue;
transmitting microwave energy into the portion of the tissue through a first apex defined by an outer shaft of the surgical instrument, thereby precoagulating the portion of the tissue;
deactivating the transmission of the microwave energy;
rotating the surgical instrument about a longitudinal axis defined by the surgical instrument, thereby positioning a second apex defined by the outer shaft adjacent the portion of tissue; and
moving a distal portion of the outer shaft of the surgical instrument along the tissue while transmitting radiofrequency energy from at least one electrode of the surgical instrument into the tissue, thereby resecting the portion of the tissue, wherein the at least one electrode is disposed closer to a second apex defined by the outer shaft than the first apex.

* * * * *